(12) United States Patent
Kleinman

(10) Patent No.: US 6,174,895 B1
(45) Date of Patent: Jan. 16, 2001

(54) 1-ARYL-3-ARYLMETHYL-1,8-NAPHTHYRIDIN-4(1H)-ONES

(75) Inventor: Edward Fox Kleinman, Pawchatuck, CT (US)

(73) Assignee: Pfizer Inc., New York, NY (US)

( * ) Notice: Under 35 U.S.C. 154(b), the term of this patent shall be extended for 0 days.

(21) Appl. No.: 09/372,735

(22) Filed: Aug. 11, 1999

Related U.S. Application Data

(60) Provisional application No. 60/096,176, filed on Aug. 11, 1998.

(51) Int. Cl.⁷ ........................ A61K 31/435; C07D 471/04
(52) U.S. Cl. .......................... 514/300; 546/122; 546/123
(58) Field of Search .................... 546/122, 123; 514/300

(56) References Cited

PUBLICATIONS

Carboni et al, J. Heterocyclic Chem., vol. 12(4), p. 743–747, 1975.*
Da Settimo et al, J. of Heterocyclic Chem., vol. 16, p. 169–174, 1979.*
Hermecz et al, J. Chem. Soc. Perkin I, p. 789–795, 1977.*

* cited by examiner

*Primary Examiner*—Bernard Dentz
(74) *Attorney, Agent, or Firm*—Peter C. Richardson; Gregg C. Benson; B. Timothy Creagan

(57) ABSTRACT

A compound of the formula

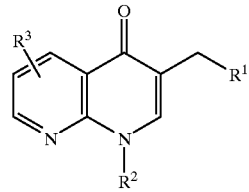

I or the pharmaceutically acceptable salt thereof, wherein $R^1$, $R^2$ and $R^3$ are as defined above, useful in the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS.

4 Claims, No Drawings

1-ARYL-3-ARYLMETHYL-1,8-NAPHTHYRIDIN-4(1H)-ONES

This application claims priority from Provisional Application No. 60/096,176 filed Aug. 11, 1998.

BACKGROUND OF THE INVENTION

This invention relates to 1-aryl-3-arylmethyl-1,8-naphthyridn4(1H)-ones that are selective inhibitors of phosphodiesterase type 4 (PDE4) and the production of tumor necrosis factor (TNF), and as such are useful in the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia, and AIDS.

This invention also relates to a method of using such compounds in the treatment of the foregoing diseases in mammals, especially humans, and to pharmaceutical compositions containing such compounds.

Since the recognition that adenosine 3',-5'-cyclic phosphate (cAMP) is an intracellular second messenger, inhibition of the phosphodiesterases has been a target for modulation and, accordingly, therapeutic intervention in a range of disease processes. More recently, distinct classes of PDE have been recognized and their selective inhibition has led to improved drug therapy. More particularly, it has been recognized that inhibition of PDE4 can lead to inhibition of inflammatory mediator release and airway smooth muscle relaxation. Thus, compounds that inhibit PDE4, but which have poor activity against other PDE types, would inhibit the release of inflammatory mediators and relax airway smooth muscle without causing cardiovascular effects or antiplatelet effects.

Recent molecular cloning has revealed a complexity and diversity of PDE4 enzymes. It is now known that there are four distinct PDE4 isozymes (A, B, C and D), each encoded for by a separate gene. Kinetic studies of human recombinant materials suggest that these four isozymes may differ in their Km's and Vmax's for hydrolysis of cAMP. Analysis of tissue distribution of PDE4 mRNAs suggests that each isozyme may be localized in a cell-specific pattern. For example, unlike human skeletal muscle, human peripheral blood leukocytes do not express PDE4C message, and guinea pig eosinophils express predominantly PDE4D message. The structural and distribution diversity of PDE4 isozymes offers an opportunity to discover an isozyme selective inhibitor that blocks the function of inflammatory cells only. Using PDE4D isozyme selective inhibitors, we have demonstrated that the PDE4D isozyme plays a key role in regulating the activation and degranulation of human eosinophils. In a primate model of asthma, PDE4D isozyme selective compounds inhibit antigen-induced pulmonary eosinophilia. Therefore, by selectively blocking the D isozyme, PDE4D inhibitors exhibit reduced side effects and retain anti-asthmatic (anti-inflammatory) efficacy.

SUMMARY OF THE INVENTION

The present invention relates to a compound of the formula

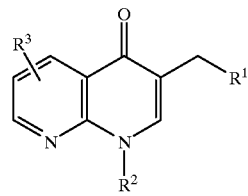

or the pharmaceutically acceptable salt thereof; wherein
$R^1$ and $R^2$ are each independently selected from the group consisting of hydrogen, $(C_1-C_6)$alkyl, $(C_3-C_7)$cycloalkyl, $(C_6-C_{10})$aryl, $(C_5-C_9)$heteroaryl and $(C_2-C_9)$heterocycloalkyl wherein the alkyl, cycloalkyl, aryl, heteroaryl or heterocycloalkyl groups are optionally substituted by halo, hydroxy, $(C_1-C_6)$alkyl, $(C_1-C_6)$alkoxy, amino, $(C_1-C_6)$alkylamino, $((C_1-C_6)$alkyl$)_2$amino, thio, $(C_1-C_6)$alkylthio, cyano, carboxy, carboxy$(C_1-C_6)$alkyl, hydroxy$(C_1-C_6)$alkyl, $(C_1-C_6)$acyl, aminosulfonyl, $(C_1-C_6)$alkylaminosulfonyl or $((C_1-C_6)$alkyl$)_2$aminosulfonyl; and
$R^3$ is hydrogen, halo, hydroxy, $(C_1-C_6)$alkyl, $(C_1-C_6)$alkoxy, amino, $(C_1-C_6)$alkylamino, $((C_1-C_6)$alkyl$)_2$amino, thio, $(C_1-C_6)$alkylthio, carboxy, carboxy$(C_1-C_6)$alkyl, hydroxy$(C_1-C_6)$alkyl, $(C_1-C_6)$acyl, aminosulfonyl, $(C_1-C_6)$alkylaminosulfonyl or $((C_1-C_6)$alkyl$)_2$aminosulfonyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g.., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_3-C_{10})$Cycloalkyl when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl etc.

$(C_2-C_9)$Heterocycloalkyl when used herein refers to azetidinyl, pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$heterocycloalkyl rings is through a carbon or a sp$^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heterocycloalkyl rings is through a carbon atom or a sp$^3$ hybridized nitrogen heteroatom.

$(C_6-C_{10})$aryl when used herein refers to phenyl or naphthyl.

Preferred compounds of formula I include those wherein $R^1$ is $(C_6-C_{10})$aryl or $(C_5-C_9)$heteroaryl.

Other preferred compounds of formula I include those wherein $R^2$ is $(C_6-C_{10})$aryl or $(C_5-C_9)$heteroaryl.

The present invention also relates to a pharmaceutical composition for the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising an amount of a compound of the formula I or a pharmaceutically acceptable salt thereof, effective in such treatment and a pharmaceutically acceptable carrier.

The present invention also relates to a method for the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising administering to said mammal an amount of a compound of the formula I or a pharmaceutically acceptable salt thereof, effective in such treatment.

The present invention also relates to a pharmaceutical composition for selective inhibition of PDE4 D isozymes which regulate the activation and degranulation of human eosinophils useful in the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising administering to said mammal a PDE4 D isozyme inhibiting effective amount of a PDE4 D isozyme inhibiting compound of the formula I or a pharmaceutically acceptable salt thereof, effective in such treatment and a pharmaceutically acceptable carrier.

The present invention also relates to a method for selective inhibition of PDE4 D isozymes which regulate the activation and degranulation of human eosinophils useful in the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising administering to said mammal a PDE4 D isozyme inhibiting effective amount of a PDE4 D isozyme inhibiting compound or a pharmaceutically acceptable salt thereof, effective in such treatment.

DETAILED DESCRIPTION OF THE INVENTION

The following reaction Schemes illustrate the preparation of compounds of the present invention. Unless otherwise indicated $R^1$, $R^2$ and $R^3$ in the reaction Schemes and the discussion that follow are defined as above.

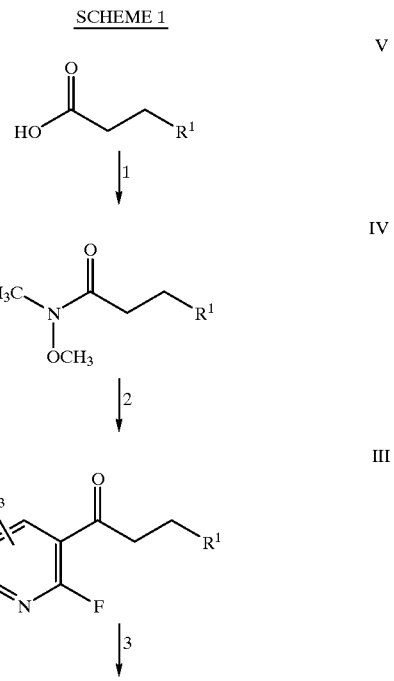

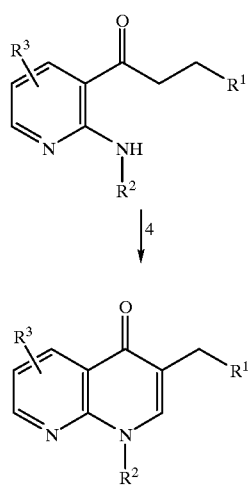

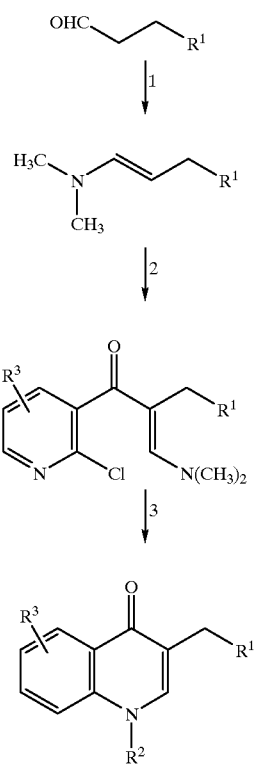

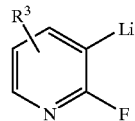

In reaction 2 of Scheme 1, the amide compound of the formula IV is converted to the corresponding pyridine compound of formula III by reacting IV with a pyridine compound of the formula in the presence of an ethereal solvent. The reaction is carried out at a temperature between about −78° C. to about 0° C., preferably about −78° C., for a time period between about 0.5 hours to about 8 hours, preferably about 4 hours.

In reaction 3 of Scheme 1, the pyridine compound of formula III is converted to the corresponding compound of formula II by reacting III with an amine of formula, $R^2$—$NH_2$, neat or in the presence of an aprotic solvent, such as dimethylformamide. The reaction is carried out at a temperature between about 70° C. to about 150° C., preferably about 100° C., for a time period between about 1 hour to about 8 hours, preferably about 2 hours.

In reaction 4 of Scheme 1, the compound of formula II is converted to the corresponding naphthyridn-4(1H)-one compound of formula I by treating II with lithium diisopropylamide in the presence of a polar aprotic solvent, such as tetrahydrofuran. Ethyl formate is added to the reaction mixture so formed at a temperature between about −78° C. to about 100° C., preferably about −78° C. to 60° C., for a time period between about 1 hour to about 5 hours, preferably about 2 hours.

In reaction 1 of Scheme 2, the aldehyde compound of formula VI is converted to the corresponding amino compound of formula VII by reacting VI with an amine of the formula, $(CH_3)_2NH$, in the presence of potassium carbonate and an aprotic solvent, such as diethyl ester. The reaction is carried out at a temperature between about −78° C. to about 60° C., preferably about −60° C. to room temperature, for a time period between about 1 hour to about 8 hours, preferably about 4 hours.

In reaction 2 of Scheme 2, the amino compound of formula VII is converted to the corresponding pyridine compound of formula VIII by reacting VII with a pyridine compound of the formula

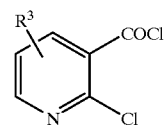

in the presence of an aprotic solvent, such as dioxane. The reaction is carried out at a temperature between about 0° C. to about 150° C., preferably about room temperature to about 80° C., for a time period between about 0.5 hours to about 2 hours, preferably about 1 hour.

In reaction 3 of Scheme 2, the pyridine compound of formula VII is converted to the corresponding naphthyridn-4(1H)-one compound of formula I by reacting VIII with an amine of the formula, $R^2NH_2$, in the presence of an aprotic basic solvent, such as pyridine. The reaction is heated to reflux for a time period between about 1 hour to about 16 hours, preferably about 2 hours. The intermediate so formed is treated with an organic base such as 1,8-diazabicyclo[5.4.0]undec-7-ene, in the presence of an ethereal solvent, such as dimethoxyethane.

In reaction 1 of Scheme 1, the carboxylic acid compound of formula V is converted to the corresponding amide compound of formula IV by reacting V with an amine salt of the formula, $H_3C$—$NH$—$OCH_3.HCl$, in the presence of 1-(3-dimethylaminopropyl)-3-ethylcarbodiimide hydrochloride, a base, such as triethylamine, and a polar aprotic solvent, such as methylene chloride. The reaction is carried out at a temperature between 0° C. to room temperature, preferably room temperature, for a time period between about 1 hour to about 32 hours, preferably about 24 hours.

The compounds of formula I that are basic in nature are capable of forming a wide variety of different salts with various inorganic and organic acids. Although such salts must be pharmaceutically acceptable for administration to humans or animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Pharmaceutically acceptable salts of amino groups include hydrochloride (preferred), hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. Cationic salts of the compounds of formula I are similarly prepared except through reaction of a carboxy group, such as when $R^3$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

For administration to humans in the curative or prophylactic treatment of inflammatory diseases, oral dosages of a compound of formula I or a pharmaceutically acceptable salt thereof (the active compounds) are generally in the range of 0.1 to 1000 mg daily, in single or divided doses, for an average adult patient (70 kg). The active compounds can be administered in single or divided doses. Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The ability of the compounds of formula I or the pharmaceutically acceptable salts thereof to inhibit $PDE_4$ may be determined by the following assay.

Inhibition of PDE4 Isozymes

Preparation of Test Compounds

Compounds are dissolved in DMSO at a concentration of $1 \times 10^{-2}$ M, or to a desired higher concentration if solubility is an issue then diluted 1:25 in water ($4 \times 10^4$ M compound, 4% DMSO). Further serial dilutions are made in 4% DMSO to achieve desired concentrations. Final DMSO concentration in assay is 1%.

In duplicate, the following are added in order to a scintillation vial (all concentrations are given as final concentrations in vial).

25 $\mu$l compound of DMSO (1%, for blank)

25 $\mu$l [$^3$H] cAMP-containing assay buffer (1 $\mu$M [$^3$H] cAMP, 50 mM Tris, 10 mM $MgCl_2$, pH 7.5)

25 $\mu$l 5'-nucleotidase (0.001 unit) (Sigma #N5880)

25 $\mu$l PDE4 isozyme (1/1200–1/2400 dilution in Prep #1)

The reaction vials are shaken and placed in a water bath (3.7° C.) for 30 minutes, at which time the reaction is stopped by adding 1 ml Dowex 1×8 resin, chloride form (1:3 slurry in distilled water). Three ml Ready Safte scintillation fluid are added directly to each vial. Mix each vial well and count radioactivity after resin has settled (approx. 4 hours at room temperature).

Data Calculation and Interpretation
Percent inhibition is determined by the formula:

$$\% \; inh = 1 - \frac{\text{avg. cpm (test compound)} - \text{avg. cpm (blank)}}{\text{avg. cpm (control (no compound)} - \text{avg. cpm (blank)}} \times 100$$

IC50 is defined as that concentration of compound which inhibits 50% of radioactivity, and is determined by Microsoft Excel or other appropriate software.

Inhibition of Eosinophil Degranulation and Activation in Human Whole Blood

Human Blood Eosinophil Degranulation and Activation Measurement

Blood Collection and Compound Incubation

One hundred ml blood is obtained from normal volunteers in Vacutainer tube #6480 (14.3 USP units sodium heparin/ml blood). Heparinized blood is pooled in 50 ml conical centrifuge tubes at 22° C. One ml blood is placed in a 12×75 mm siliconized glass tube containing 1 ul DMSO or 1 ul test compound in triplicate. After mixing, tubes are placed in a shaking water bath at 37° C. for 15 minutes. One ul PGE1 in DMSO is added to all tubes to give a final concentration of 1 uM. After mixing, 100 ul PBS (negative control) or Sephadex G-15 beads in PBS (8.25–16.5 mg/ml final concentration) is added to tubes. After mixing, all tubes are incubated in a shaking water bath at 37° C. for 1–2 hours.

Preparation of Plasma Samples

At the end of incubation, 20 ul of 15% EDTA in PBS is added to each assay tube. After mixing, the samples are centrifuged at 2,000 rpm (Sorvall 6000B centrifuge) at 22° C. for 5 minutes.

EDN (or EPX) and LTE4 Measurements and the Effect of Compounds

All plasma samples are tested for EDN (eosinophil derived neurotoxin) and LTE4 (leukotriene E4) levels. Extensive studies suggest that Sephadex beads trigger cosinophil-mediated EDN and LTE4 release in human whole blood. The levels of EDN and LTE4 are determined by a RIA (Kabi Pharmacia Diagnostics) and EIA (Cayman Chemical), respectively. EDN and LTE4 levels are calculated by comparison to a standard curve using Microsoft Excel or other appropriate software. Percent of control EDN or LTE4 release is calculated by:

% Control EDN=[EDN (compound)-EDN(blank)]/[EDN(total)-EDN(blank)]

% Control LTE4=[LTE4(compound)-LTE4(blank)]/[LTE4(total)-LTE4(blank)]

where the blank is the level of EDN or LTE4 in the absence of Sephadex beads and the total is the level of EDN or LTE4 in the presence of Sephadex beads. An $IC_{30}$ or $IC_{50}$ value is defined as the concentration of a compound that inhibits specific EDN or LTE4 release by 30 or 50%, respectively.

Inhibition of Pulmonary Eosinophilia

To evaluate these compounds for pulmonary efficacy, we have used a well-characterized monkey model of asthma (Turner et al., *Am. J. Respir. Crit. Care Med.* 149, 1153–1159, 1994). Exposure of atopic *Macaca fascicularis* monkeys to antigen causes a significant influx of inflammatory cells observed in the bronchoalveolar (BAL) fluid of these monkeys at 4–24 hours post antigen challenge. In this model, PDE4D isozyme selective compounds given subcutaneously significantly inhibit pulmonary eosinophil infiltration by 59–76% at 24 h post antigen challenge. These compounds, however, do not affect neutrophil or lymphocyte infiltration, demonstrating selective inhibition of the eosinophil response by these compounds.

Inhibition of TNF Production in Isolated Human-Monocytes

The ability of the compounds I or the pharmaceutically acceptable salts thereof to inhibit the production TNF and, consequently, demonstrate their effectiveness for treating disease involving the production of TNF is shown by the following in vitro assay:

Peripheral blood (100 mls) from human volunteers is collected in ethylenediaminetetraacetic acid (EDTA). Mononuclear cells are isolated by FICOLL/Hypaque and washed three times in incomplete HBSS. Cells are resuspended in a final concentration of $1 \times 10^6$ cells per ml in pre-warmed RPMI (containing 5% FCS, glutamine, pen/step and nystatin). Monocytes are plated as $1 \times 10^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 ml) are then added to the cells at 3–4 concentrations each and incubated for 1 hour. LPS (10 ml) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis.

The present invention is illustrated by the following examples, but it is not limited to the details thereof.

EXAMPLE 1

1-(4-Fluorophenyl)-3-(phenylmethyl)-1,8-naphthyridin-4(1H)-one

A solution of 2.67 mL (1.98 grams, 19.6 mmol) of diisopropylamine in 30 mL of tetrahydrofuran was cooled to −78° C. and treated dropwise with 7.80 mL (19.5 mmol) of a solution of 2.5 M n-butyllithium in hexane. After stirring for 5 minutes, a solution of 2.16 grams (6.53 mmol) of the compound of Preparation 11 in 8 mL of tetrahydrofuran was added dropwise, and the resulting red mixture was allowed to stir for 5 minutes before being treated with 0.890 mL (0.816 grams, 110 mmol) of freshly distilled ethyl formate (from calcium hydride). The mixture was allowed to warm to rt (as the dry ice bath melted), stirred for 2 hours at room temperature, and heated to 60° C. for 2 hours. The cooled mixture was quenched by the addition of 5 mL of saturated aqueous ammonium chloride solution and partitioned between 150 mL of ethyl acetate and 100 mL of saturated aqueous ammonium chloride solution. The separated organic layer was washed with brine (1×100 mL), dried (MgSO$_4$), and evaporated to give 3.74 grams of a yellow solid. Purification by flash chromatography (preabsorption technique) using 50% EtOAc-hexane as eluant gave 1.5 grams of a pale yellow solid which was recrystallized from ethyl acetate to afford 1.3 grams (59% yield) of the title compound, mp 208–209° C. Anal. Calcd for $C_{21}H_{15}N_2OF$: C, 76.35; H, 4.58; N, 8.48. Found: C, 76.13; H, 4.59; N, 8.47.

EXAMPLES 2–6

The compounds of Examples 2–6 were prepared according to the procedure of Example 1 substituting the indicated substrate for the compound of Preparation 11.

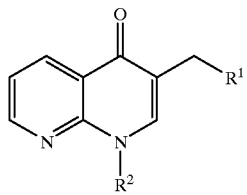

| Example | Substrate | R¹ | R² | M.P. (° C.) | Spectral or Analytical Data |
|---|---|---|---|---|---|
| 2 | Cmpd. of Prep. 12 | phenyl | 3-bromophenyl | 166–167 | $^1$H NMR(CDCl$_3$) d 3.93(2H, s), 7.20–7.62(11H, m), 8.60(1H, dd, J=2, 5Hz), 8.77(1H, dd, J=2, 8Hz); AP$_c$I MS (m/e) 391 and 393(M$^+$+1). |
| 3 | Cmpd. of Prep. 13 | phenyl | 3-iodophenyl | 181–182 | Anal. Calcd for C$_{21}$H$_{15}$N$_2$OI: C, 57.55; H, 3.45; N, 6.39. Found: C, 57.43; H, 3.26; N, 6.68. |
| 4 | Cmpd. of Prep. 14 | phenyl | cyclohexyl | 198–199 | Anal. Calcd for C$_{21}$H$_{22}$N$_2$O: C, 79.21; H, 6.96; N, 8.80. Found: C, 78.99; H, 6.96; N, 8.85. |
| 5 | Cmpd. of Prep. 15 | 4-bromophenyl | 4-fluorophenyl | 186–187 | Anal. Calcd for C$_{21}$H$_{14}$N$_2$OFBr: C, 61.63; H, 3.45; N, 6.84. Found: C, 61.73; H, 3.46; N, 6.97. |
| 6 | Cmpd. of Prep. 16 | 4-(NMe$_2$)phenyl | 4-fluorophenyl | 147–148 | Anal. Calcd for C$_{23}$H$_{20}$N$_3$OF: C, 73.98; H, 5.40; N, 11.25. Found: C, 73.70; H, 5.42; N, 11.05. |

EXAMPLE 7

3-[(4-Acetylphenyl)methyl]-1-(4-fluorophenyl)-1,8-naphthyridin-4(1H)-one

A mixture of 266 mg (0.650 mmol) of the compound of Example 5, 0.242 mL (0.259 grams, 0.716) of (1-ethoxyvinyl)tributyltin, 8 mg (0.007 mmol) of tetrakis (triphenylphosphine)palladium(0), and 2 mL of benzene was heated for 16 hours at 80° C. At this time an additional 0.120 mL of (1-ethoxyvinyl)tributyltin and 7 mg of tetrakis (triphenylphosphine)palladium(0) were added, and heating was continued for another 16 hours. The cooled mixture was filtered through celite rinsing using ethyl acetate as a rinse, and the filtrate was washed with aqueous 1 N hydrochloric acid solution, brine (1×50 mL), dried (MgSO4), and evaporated to give 700 mg of a white solid. Recrystallization from EtOAc-hexane afforded 85 mg (35% yield) of the title compound as a white powder, mp 227–229° C. $^1$H NMR (CDCl$_3$) d 2.55 (3H, s), 3.97 (2H, s), 7.18–7.88 (10H, m), 8.60 (1H, dd, J=2, 4 Hz), 8.75 (1H, dd, J=2, 7 Hz); $AP_{Cl}$ MS (m/e) 373 ($M^++1$).

EXAMPLE 8

1-(4-Fluorophenyl)-3-[[4-(1-hydroxyethyl)phenyl] methyl-]-1,8-naphthyridin-4(1H)-one A solution of 49 mg (0.13 mmol) of the compound of Example 7 in 7 mL of methanol was cooled to 0° C. and treated with 5.0 mg (0.13 mmol) of sodium borohydride. After stirring for 1 hour at 0° C. and 2 hours at room temperature, the mixture was quenched by the addition of 2 mL of water. The mixture was concentrated to remove methanol and the residue was partitioned between 50 mL of ethyl acetate and 50 mL of water. The separated organic layer was washed with brine (1×50 mL), dried ($MgSO_4$), and evaporated to give 22 mg of the title compound as a white solid, mp 197–198° C. Anal. Calcd for $C_{23}H_{19}N_2O_2F$: C, 73.78; H, 5.11; N, 7.48. Found: C, 73.41; H, 5.20; N, 7.41.

EXAMPLE 9

1-(3-Dimethylamino)phenyl-3-(phenylmethyl)-1,8-naphthyridin-4(1H)-one

A mixture of 180 mg (0.46 mmol) of the compound of Example 2, 0.087 mL (71 mg, 0.50 mmol) of tris (dimethylamino)borane, 8 mg (0.009 mmol) of tris (dibenzylideneacetone)dipalladium(0), 6 mg (0.018 mmol) of tri-o-tolylphosphine, 61 mg (0.63 mmol) of sodium t-butoxide, and 5 mL of toluene was heated for 3 hours at 100° C. The cooled mixture was diluted with 50 mL of ethyl acetate, washed with brine (1×50 mL), dried ($Na_2SO_4$), and evaporated. The residue was found to contain unreacted starting material and was thus retreated for 16 hours in an identical manner to that described above. After work-up, the crude product (150 mg) was purified by flash chromatography using a 50% EtOAc-hexane eluant to give 72 mg of an oil which solidified on standing. Recrystallization from ethyl acetate-hexane afforded 44 mg (27% yield) of the title compound as white crystals, mp 129–130° C. $^1$H NMR ($CDCl_3$) d 2.96 (6H, s), 3.94 (2H, s), 6.62–6.80 (3H, m), 7.15–7.39 (7H, m), 7.57 (1H, s), 8.62 (1H, dd, J=2, 4 Hz), 8.76 (1H, dd, J=2, 8 Hz); $AP_{Cl}$ MS (m/e) 356 ($M^++1$).

EXAMPLE 10

1-(3-Chlorophenyl)-3-(phenylmethyl)-1,8-naphthyridin-4(1H)-one

A mixture of 185 mg (0.603 mmol) of the compound of Preparation 20, 0.0980 mL (118 mg, 0.926 mmol) of 3-chloroaniline, and 3 mL of pyridine was heated for 2 hours at reflux. The cooled mixture was partitioned between ethyl acetate and aqueous 1 N hydrochloric acid solution, and the separated organic layer was washed with brine, dried ($MgSO_4$), and evaporated to give 120 mg of a solid. This was combined directly with 0.0700 mL (71.2 mg, 0.468 mmol) of 1,8-diazabicyclo[5.4.0]undec-7-ene in 2 mL of DME, and the mixture was heated for 3 hours at 60° C., cooled, and partitioned between 50 mL of ethyl acetate and 50 mL of saturated aqueous ammonium chloride solution. The separated organic layer was washed with brine (1×50 mL), dried ($MgSO_4$), and evaporated to give 151 mg of a yellow semi-solid. Purification by flash chromatography using a 25% EtOAc-hexane eluant afforded 53 mg (49% yield) of the title compound as a white solid, mp 169.5–171° C. Anal. Calcd for $C_{21}H_{15}N_2OCl$: C, 72.73; H, 4.36; N, 8.08. Found: C, 72.71; H, 4.40; N, 8.11.

EXAMPLE 11 trans-1-(4-Fluorophenyl)-3-[[4-(2-hydroxy-2-propyl)]cyclohexyl]methyl-1,8-naphthyridin-4(1H)one Into a 10 mL teflon tube was placed a mixture of 49 mg (0.096 mmol) of the compound of Preparation 18, 1 mL of tetrahydrofuran, and 25 µL of HF.pyridine complex (Aldrich). The contents were heated for 4 days at 45° C., at which time an additional 1 mL of tetrahydrofuran and 25 µL of HF.pyridine complex were added. Heating was then continued at 45° C. for an additional 3 days. The cooled mixture was treated with excess solid sodium hydrogencarbonate, diluted with ethyl acetate, and filtered through a plug of glass wool. The filtrate was evaporated to give 78 mg of a yellow solid, which was purified by flash chromatography using a 20–75% ethyl acetate-hexane eluant to give 17 mg (45%) of the title compound as a white solid after trituration with ether, mp 207.5–209° C. $^1$H NMR ($CDCl_3$) d 0.91–1.28 (6H, m), 1.12 (6H, s), 1.79–1.88 (4H, m), 2.43 (2H, d, J=7 Hz), 7.20–7.41 (5H, m), 7.60 (1H, s), 8.58 (1H, dd, J=2, 4 Hz), 8.74 (1H, dd, J=2, 8 Hz); $AP_{Cl}$ MS (m/e) 395 ($M^++1$).

Preparation 1 trans-1-Bromomethyl-4-(2-hydroxy-2-propyl) cyclohexane

A mixture of 1.994 grams (11.57 mmol) of trans-p-menthane-7,8diol (for preparation, see: Ohloff, G.; Giersch, W. Helv. Chim. Acta., 1980, 63, 76), 3.035 grams (11.57 mmol) of triphenylphosphine, and 20 mL of benzene was chilled in an ice bath and treated portionwise with 2.060 grams (11.57 mmol) of N-bromosuccinimide. The ice bath was removed and the mixture was stirred for 16 hours at room temperature. The mixture was diluted with 50 mL of hexane and the solids were removed by filtering sequentially through celite and filter paper. The filtrate was washed with 0.5 $Na_2S_2O_3$ solution (2×100 mL), 1 N sodium hydroxide solution (1×50 mL), brine (1×50 mL), dried ($Na_2SO_4$), and evaporated. The residue was diluted with hexane and filtered to remove triphenylphospineoxide. The residue was purified by flash chromatography using a 10–50% EtOAc-hexane eluant to give 3.382 grams (88%) of the title compound an oil. $^1$H NMR ($CDCl_3$) d 0.93–1.28 (6H, m), 1.15 (6H, s), 1.58 (1H, br s), 1.83–2.00 (4H, m), 3.27 (2H, d, J=7 Hz).

Preparation 2 trans-1-Bromomethyl-4-(2-t-butyldimethylsilyloxy-2-propyl)-cyclohexane

A solution of 249 mg (1.06 mmol) of the compound of Preparation 2 in 2 mL of ethane was treated with 0.246 mL (227 mg, 2.18 mmol) of 2,6-lutidine followed by 0.365 mL (419 mg, 1.59 mmol) of TBDSOTf. The mixture was stirred for 3 hours at room temperature, concentrated, and partitioned between 50 mL of hexane and 50 mL of water. The aqueous layer was separated and the organic layer was washed with aqueous 1 N hydrochloric acid solution (2×50 mL), saturated sodium hydrogencarbonate solution (1×25 mL), brine (1×25 mL), dried ($MgSO_4$), and evaporated to give 411 mg of a clear oil. Purification by flash chromatography using a hexane eluant afforded 369 mg (100%) of the title compound as an oil. $^1$H NMR ($CDCl_3$) d 0.05 (6H, s), 0.84 (9H, s), 0.85 (6H, s), 0.93–1.20 (6H, m), 1.82–1.97 (4H, m), 3.26 (2H, d, J=6 Hz).

Preparation 3 trans-N-Methoxy-N-methyl-4-(2-t-butyldimethylsilyloxy-2-propyl)-cyclohexanepropanamide To a –78° C. solution of lithium diisopropylamide, prepared by the addition of 39.2 mL (98.0 mmol) of 2.5 n-BuLi solution in hexane to 13.7 mL (9.92 grams, 98.0 mmol) of diisopropylamine in 200 mL of THF, was added 2.80 mL (2.94 grams, 49.0 mmol) of acetic acid (distilled from KMnO$_4$) dropwise at such a rate that the exotherm did not exceed −60 ° C. When the addition was complete, the resulting suspension was treated with 17.1 mL (17.6 grams, 98.0 mmol) of hexamethylphosphoramide to give a light brown solution to which was added 8.56 grams (24.5 mmol) of the compound of Preparation 2 in 5 mL of tetrahydrofuran. The mixture was stirred at −78° C. for 1 hr, warmed to room temperature, and refluxed for 16 hours. The cooled mixture was quenched by the addition of 300 mL of saturated ammonium chloride solution and extracted with 300 mL of ethyl acetate. The organic layer was washed with brine (1×300 mL), dried (MgSO$_4$), and evaporated to give 9.78 grams (>100%) of crude trans-4-(2-t-butyldimethylsilyloxy-2-propyl)-cyclohexanepropanoic acid as an oil.

A mixture of the acid above, 3.19 grams (32.7 mmol) of N,O-dimethylhydroxylamine hydrochloride, 6.28 grams (32.7 mmol) of DEC.HCl, and 250 mL of methylene chloride was treated with 8.30 mL (32.7 mmol) of triethylamine, and the resulting mixture was allowed to stir for 16 hours at room temperature. The solvent was evaporated and the residue was partitioned between 300 mL of ethyl acetate and 300 mL of aqueous 1 N hydrochloric acid solution. The organic layer was separated, combined with a 200 mL backwash of the aqueous layer, washed with saturated sodium hydrogencarbonate solution (1×400 mL), brine (1×300 mL), dried (MgSO$_4$), and evaporated to give 7.81 grams of a brown oil. Purification by flash chromatography using 20% ethyl acetate-hexane as eluant afforded 1.08 grams (10%) of the title compound as a brown oil. $^1$H NMR (CDCl$_3$) d 0.04 (6H, s), 0.83 (9H, s), 0.83–1.18 (6H, m), 1.12 (6H, s), 1.50 (2H, br q, J=7 Hz), 1.77–1.82 (4H, m), 2.41 (2H, br t, J=8 Hz), 3.16(3H, s), 3.67 (3H, s).

Preparation 4

N-Methoxy-N-methyl-3-phenylpropanamide

A suspension of 10.2 grams (68.1 mmol) of hydrocinnamic acid, 14.4 grams (74.9 mmol) of 1-ethyl-3-(3-dimethylaminopropyl)carbodiimide hydrochloride, 7.31 grams (74.9 mmol) of N,O-dimethylhydroxylamine hydrochloride in 250 mL of methylene chloride was cooled to 0° C. and treated with 19.1 mL (13.9 grams, 136 mmol) of triethylamine. The mixture was stirred for 16 hours with slow warming to rt and was then concentrated. The residue was taken up in 250 mL of ethyl acetate, washed with aqueous 1N hydrochloric acid solution (2×150 mL), saturated aqueous sodium hydrogencarbonate solution (2×100 mL), brine (1×100 mL), dried (Na$_2$SO$_4$), and evaporated to give 13.11 grams (99%) of the title compound as an oil. Anal. Calcd for C$_{11}$H$_{15}$NO$_2$: C, 68.37; H, 7.82; N, 7.25. Found: C, 68.65; H, 8.11; N, 7.18.

Preparations 5 and 6

The compounds of Preparations of 5 and 6 were prepared as oils according to the procedure of Preparation 4 substituting 3-(4-bromophenyl)propanoic acid (for preparation, see: Adamczyk et al. *J. Org. Chem.*, 1984, 49, 4226) and 3-(4-dimethylaminophenyl)propanoic acid (for preparation, see: Lightner, D. A. et al. *Tetrahedron*, 1991, 47, 9759), respectively, for hydrocinnamic acid. The compound of Preparation 6 was further purified by flash chromatography using 30–50% EtOAc-hexane as eluant.

| Preparation | Structure | Spectral or Analytical Data |
|---|---|---|
| 5 | 4-Br-C$_6$H$_4$-CH$_2$CH$_2$-CONMe(OMe) | $^1$H NMR(CDCl$_3$) d 2.70(2H, t, J=8Hz), 2.89(2H, t, J=8Hz), 3.15(3H, s), 3.59(3H, s), 7.09(2H, d, J=8Hz), 7.38(2H, d, J=8Hz); AP$_c$I MS (m/e) 272 and 274(M$^+$+1). |
| 6 | 4-Me$_2$N-C$_6$H$_4$-CH$_2$CH$_2$-CONMe(OMe) | $^1$H NMR(CDCl$_3$) d 2.71(2H, t, J=8Hz), 2.85(2H, t, J=8Hz), 2.90(6H, s), 3.17(3H, s), 3.60(3H, s), 6.69(2H, d, J=8Hz), 7.22(2H, d, J=8Hz); AP$_c$I MS (m/e) 237(M$^+$+1). |

Preparation 7

1-(2-Fluoro-3-pyridinyl)-3-phenyl-1-propanone

A solution of 2.33 mL (1.99 grams, 17.8 mmol) of diisopropylamine in 30 mL of tetrahydrofuran was cooled to −78° C. and treated dropwise with 7.12 mL (17.8 mmol) of a solution of 2.5 M n-butyllithium in hexane. When the addition was complete, the mixture was stirred for 5 minutes at −78° C. and treated dropwise with 1.53 mL (1.36 grams, 17.8 mmol) of freshly distilled 2-fluoropyridine. After the addition was complete, the yellow mixture was stirred for 15 minutes at −78° and treated dropwise with a solution of 3.44 grams (17.8 mmol) of the compound of Preparation 4 in 2 mL of THF. The mixture was stirred for 4 hours at −78° C. and then quenched by the addition of 5 mL of saturated aqueous ammonium chloride solution. After warming to room temperature, the mixture was partitioned between 175 mL of ethyl acetate and 150 mL of saturated aqueous ammonium chloride solution. The separated organic later was washed with brine (100 mL), dried (MgSO4), and evaporated to 3.49 grams of an orange oil. Purification by flash chromatography using a 25% EtOAc-hexane eluant afforded 940 mg (23%) of the title compound as a yellow oil. $^1$H NMR (CDCl$_3$) d 3.05 (2H, t, J=7 Hz), 3.32–3.64 (2H, m), 7.17–7.33 (6H, m), 8.29–8.38 (2H, m); AP$_c$I MS (m/e) 229 (M$^+$).

Preparations 8–10

The compounds of Preparations 8–10 were prepared according to the procedure of Preparation 7 substituting the indicated substrate for the compound of Preparation 4.

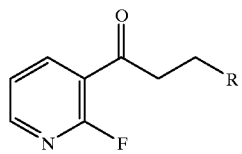

| Prep. | Substrate | R | M.P. (° C.) | Spectral or Analytical Data |
|---|---|---|---|---|
| 8 | Cpd. of Prep. 5 | (4-bromophenyl) | 68–69 | Anal. Calcd for $C_{14}H_{11}NOBrF$: C, 54.57; H, 3.60; N, 4.55; Found: C, 54.32; H, 3.76; N, 4.38. |
| 9 | Cpd. of Prep. 6 | (4-dimethylaminophenyl) | oil | $^1H$ NMR(CDCl$_3$) d 2.90(6H, s), 2.95(2H, t, J=8Hz), 3.27–3.32(2H, m), 6.68(2H, d, J=8Hz), 7.11(2H, d, J=8Hz), 7.29–7.32(1H, m), 8.23–8.37(2H, m); AP$_c$I MS (m/e) 273(M$^+$+1). |
| 10 | Cpd. of Prep. 3 | (trans-4-OTBDS cyclohexyl) | oil | $^1H$ NMR(CDCl$_3$) d 0.04(6H, s), 0.84(9H, s), 0.84–1.18(6H, m), 1.13(6H, s), 1.59(2H, br q, J=7Hz), 1.75–1.87(4H, m), 2.99–3.03(2H, m), 7.28–7.33(1H, m), 8.26–8.38(2H, m). |

Preparation 11

1-[2-(4-Fluoroanilino)-3-pyridinyl]-3-phenyl-1-propanone

A mixture of 3.01 grams (13.1 mmol) of the compound of Preparation 7 and 5.00 mL (5.86 grams, 52.8 mmol) of p-fluoroaniline was heated for 2 hours at 100° C. The excess aniline was removed by distillation, and the residue was dissolved in ethyl acetate, washed with water, brine (1×50 mL), dried (MgSO$_4$), and evaporated to give 4.1 grams of a yellow solid, which was then refluxed for 1 hour in aqueous 1 N hydrochloric acid solution. The cooled mixture was extracted with ethyl acetate, and the combined extracts were washed with brine, dried (MgSO4), and evaporated to give 3.6 grams (86% yield) of the title compound as a yellow solid. The analytical sample was prepared by recrystallization from hexane, mp 100.5–102° C. Anal. Calcd for $C_{20}H_{17}N_2OF$: C, 74.98; H, 5.35; N, 8.74. Found: C, 74.95; H, 5.40; N, 8.78.

Preparations 12–17

The compounds of Preparations 12–17 were prepared according to procedure of Preparation 11 substituting the indicated substrate for the compound of Preparation 7 and the indicated aniline or amine for p-fluoroaniline.

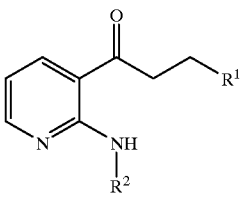

| Preparation | Substrate | R$^1$ | R$^2$ | M.P. (° C.) | Spectral or Analytical Data |
|---|---|---|---|---|---|
| 12 | Cmpd. of Prep. 7 | phenyl | 3-bromophenyl | 95–96 | Anal. Calcd for $C_{20}H_{17}N_2OBr$: C, 63.01; H, 4.49; N, 7.35. Found: C, 62.91; H, 4.21; N, 7.27. |

-continued

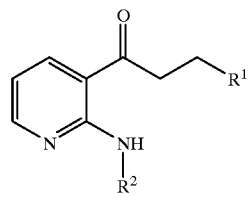

| Preparation | Substrate | R¹ | R² | M.P. (° C.) | Spectral or Analytical Data |
|---|---|---|---|---|---|
| 13 | Cmpd. of Prep. 7 | phenyl | 3-iodophenyl | 104–105 | Anal. Calcd for $C_{20}H_{17}N_2OI$: C, 56.09; H, 4.00; N, 6.54. Found: C, 56.42; H, 3.99; N, 6.73. |
| 14 | Cmpd. of Prep. 7 | phenyl | cyclohexyl | semi-solid | $^1$H NMR(DMSO-d$^6$) d 1.18–1.96(10H, m), 2.88(2H, t, J=7Hz), 3.34(2H, t, J=7Hz), 3.90–4.05(1H, m), 6.65–6.75(1H, m), 7.14–7.17(1H, m), 7.21–7.24(4H, m), 8.22(1H, dd, J=2, 8Hz), 8.37–8.52(1H, m), 9.30(1H, br s); AP$_c$I MS (m/e) 309(M$^+$+1). |
| 15 | Cmpd. of Prep. 8 | 4-bromophenyl | 4-fluorophenyl | 120.5–122 | Anal. Calcd for $C_{20}H_{16}N_2OFBr$: C, 60.17; H, 4.04; N, 7.02. Found: C, 60.41; H, 4.03; N, 6.96. |
| 16 | Cmpd. of Prep. 9 | 4-(NMe$_2$)phenyl | 4-fluorophenyl | 128–129 | $^1$H NMR(CDCl$_3$) d 2.91(6H, s), 2.96(2H, t, J=7.5Hz), 3.26(2H, t, J=7.5Hz), 6.66–7.13(7H, m), 7.62(2H, dd, J=5, 8Hz), 8.10(1H, dd, J=2, 8Hz), 8.33(1H, dd, J=2, 5Hz); AP$_c$I MS (m/e) 364(M$^+$+1). |
| 17 | Cmpd. of Prep. 10 | trans-4-(OTBDS-substituted) cyclohexyl | 4-fluorophenyl | oil | $^1$H NMR(CDCl$_3$) d 0.04(6H, s), 0.84(s, 9H), 0.84–1.20(6H, m), 1.12(6H, s), 1.55–1.70(2H, m), 1.79–1.80(4H, m), 2.97–3.07(2H, m), 6.69–8.40(8H, m); AP$_c$I MS (m/e) 499(M$^+$+1). |

Preparation 18 trans-3-[[4-(2-t-Butyldimethylsilyloxy-2-propyl)]cyclohexyl]methyl-1-(4-fluorophenyl)-1,8-naphthyridin-4(1H)-one To a −78° C. solution of lithium diisopropylamide, prepared by adding 1.41 mL (3.52 mmol) 2.5 M n-butyl lithium solution in hexane to a solution of 0.493 mL (0.356 grams, 3.52 mmol) of diisopropylamine in 7 mL of tetrahydrofuran, was added dropwise a solution of 0.439 grams (0.880 mmol) of the compound of Preparation 17. When the addition was complete, the resulting orange mixture was treated with 0.284 ml (0.261 grams, 3.52 mmol) of ethyl formate followed by 0.306 mL (0.315 grams, 1.76 mmol) of hexamethylphosphoramide. The resulting red mixture was allowed to warm to rt over 1 h and was then heated to reflux for 2 hours. The cooled mixture was quenched by the addition of 50 mL of saturated aqueous ammonium chloride solution and the organic layer was extracted with ethyl acetate (2×100 mL). The combined organic layers were washed with brine (1×100 mL), dried (MgSO$_4$), and evaporated to give a dark oil, which was purified by by flash chromatography using a 20–50% ethyl acetate eluant to afford 123 mg (27%) of the title compound as a foam. $^1$H NMR (CDCl$_3$) d 0.00 (6H, s), 0.80 (9H, s), 0.85–1.05 (6H, m), 1.08 (6H, s), 1.73–1.83 (4H, m) 2.41 (2H, d, J=7 Hz), 7.19–7.40 (5H, m), 7.58 (1H, s), 8.57 (1H, dd, J=2, 4 Hz), 8.73 (1H, dd, J=2 8 Hz); AP$_C$I MS (m/e) 509 (M$^+$+1), 377 (base).

Preparation 19

N,N-Dimethyl-3-phenyl-(E)-1-propene-1-amine

A mixture of 19.6 mL (20.0 grams, 149 mmol) of cinnamaldehyde, 40.6 grams (298 mmol) of potassium carbonate, and 150 mL of ether was cooled to −60° C. and treated with a prechilled (−78° C.) solution of 17.8 mL (13.5 grams, 300 mmol) of liquid dimethylamine, condensed from the gas at −78° C., in 20 mL of ether. After stirring for 0.5 hours at −60° C., the mixture was allowed to slowly warm to room temperature and then stirred for an additional 3 hours. The mixture was filtered, concentrated, and distilled to give 10.2 grams (42% yield) of the title compound as a yellow liquid, bp 95–100° C./2.8–3.0 Torr. The liquid slowly polymerized on standing and was used directly. $^1$H NMR (CDCl$_3$) d 2.57 (6H, s), 3.30 (2H, d, J=7 Hz), 4.35 (1H, dt, J=7, 14 Hz), 5.99 (1H, dt, J=1, 14 Hz), 7.15–732 (5H, m).

Preparation 20

1-(2-Chloro-3-pyridinyl)-3-(dimethylamino)-2-(phenylmethyl)-2-propen-1-one

To a mixture of 1.23 grams (7.73 mmol) of the compound of Preparation 19, 1.60 mL (1.16 grams, 11.5 mmol) of triethylamine, and 10 mL of dioxane was added 1.36 grams (7.73 mmol) of 2-chloronicotinoyl chloride. The resulting orange suspension was stirred for 0.5 hours at room temperature and then heated for 0.5 hours at 80° C. The cooled mixture was partitioned between 100 mL of ethyl acetate and 100 mL of saturated aqueous sodium hydrogencarbonate solution, and the separated organic layer was washed with saturated aqueous sodium hydrogencarbonate solution (1×50 mL), brine (1×50 mL), dried (MgSO$_4$), and evaporated to 1.6 grams of an orange solid. Recrystallization from ice cold hexane gave 170 mg (7% yield) of the title compound, mp 115–120° C. $^1$H NMR (DMSO-d$^6$) d 2.89 (6H, s), 3.80–4.02 (2H, m), 6.82 (1H, br s), 7.11–7.44 (6H, m), 7.20 (1H, d, J=7 Hz), 8.40 (1H, dd, J=1.5, 4.5 Hz).

What is claimed is:

1. A compound of the formula

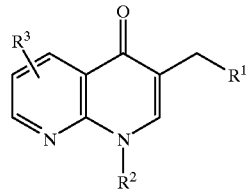

or the pharmaceutically acceptable salt thereof; wherein

R$^1$ is selected from the group consisting of hydrogen, (C$_1$–C$_6$)alkyl, (C$_3$–C$_7$)cycloalkyl, (C$_6$–C$_{10}$)aryl, (C$_5$–C$_9$)heteroaryl and (C$_2$–C$_9$)heterocycloalkyl wherein the alkyl, cycloalkyl, aryl, heteroaryl or heterocycloalkyl groups are optionally substituted by halo, hydroxy, (C$_1$–C$_6$)alkyl, (C$_1$–C$_6$)alkoxy, amino, (C$_1$–C$_6$)alkylamino, ((C$_1$–C$_6$)alkyl)$_2$amino, thio, (C$_1$–C$_6$)alkylthio, cyano, carboxy, carboxy(C$_1$–C$_6$)alkyl, hydroxy(C$_1$–C$_6$)alkyl, (C$_1$–C$_6$)acyl, aminosulfonyl, (C$_1$–C$_6$)alkylaminosulfonyl or ((C$_1$–C$_6$)alkyl)$_2$aminosulfonyl;

R$^2$ is (C$_6$–C$_{10}$)aryl or (C$_5$–C$_9$)heteroaryl; and

R$^3$ is hydrogen, halo, hydroxy, (C$_1$–C$_6$)alkyl, (C$_1$–C$_6$)alkoxy, amino, (C$_1$–C$_6$)alkylamino, ((C$_1$–C$_6$)alkyl)$_2$amino, thio, (C$_1$–C$_6$)alkylthio, carboxy, carboxy(C$_1$–C$_6$)alkyl, hydroxy(C$_1$–C$_6$)alkyl, (C$_1$–C$_6$)acyl, aminosulfonyl, (C$_1$–C$_6$)alkylaminosulfonyl or ((C$_1$–C$_6$)alkyl)$_2$aminosulfonyl.

2. A compound according to claim 1, wherein R$^1$ is (C$_6$–C$_{10}$)aryl or (C$_5$–C$_9$)heteroaryl.

3. A pharmaceutical composition for the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising an amount of a compound of claim 1 or a pharmaceutically acceptable salt thereof, effective in such preventions or treatment and a pharmaceutically acceptable carrier.

4. A method for the treatment of respiratory, allergic, rheumatoid, body weight regulation, inflammatory and central nervous system disorders such as asthma, chronic obstructive pulmonary disease, adult respiratory diseases syndrome, toxic shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising administering to said mammal an amount of a compound of claim 1 or a pharmaceutically acceptable salt thereof, effective in such treatment.

* * * * *